United States Patent [19]
Bauer et al.

[11] Patent Number: 5,772,655
[45] Date of Patent: Jun. 30, 1998

[54] MEDICAL INSTRUMENT WITH A TILTING DISTAL END

[75] Inventors: Otmar Bauer, Kludenbach; Manfred Boebel, Oetisheim, both of Germany

[73] Assignee: Richard Wolf GmbH, Knittlingen, Germany

[21] Appl. No.: 648,528

[22] Filed: May 13, 1996

[30] Foreign Application Priority Data

May 19, 1995 [DE] Germany ................. 195 183 88.6

[51] Int. Cl.[6] .................................................. A61B 17/02
[52] U.S. Cl. ............................. 606/1; 600/201; 600/215
[58] Field of Search ........................... 606/1, 45–52, 606/205–208; 128/751; 600/201, 210, 215, 226, 227

[56] References Cited

U.S. PATENT DOCUMENTS

| | | | |
|---|---|---|---|
| 4,763,669 | 8/1988 | Jaeger | 128/751 |
| 4,880,015 | 11/1989 | Nierman . | |
| 5,064,424 | 11/1991 | Bitrolf | 606/46 |
| 5,192,280 | 3/1993 | Parins | 606/48 |
| 5,209,747 | 5/1993 | Knoepfler | 606/205 |
| 5,289,817 | 3/1994 | Williams et al. . | |
| 5,314,445 | 5/1994 | Heidmueller et al. | 606/205 |
| 5,330,502 | 7/1994 | Hassler et al. | 606/205 |
| 5,520,678 | 5/1996 | Heckele et al. | 606/1 |

FOREIGN PATENT DOCUMENTS 0 557 806 A2 9/1993 European Pat. Off. .
WO 95/11630 5/1995 WIPO .

Primary Examiner—Michael Peffley
Attorney, Agent, or Firm—Panitch Schwarze Jacobs & Nadel, P.C.

[57] ABSTRACT

The invention relates to a medical instrument with a distal end piece which is connected to a holder running through a shank and on operation of a handle, can be adjusted from a rest position into an operating position by tilting relative to the longitudinal axis of the instrument. The end piece and the holder lie facing one another in a plane running inclined to the longitudinal axis of the instrument as well as perpendicular to it, and are connected with a fastening element which forms an axis perpendicular to said plane, about which the end piece is pivotable relative to the holder.

8 Claims, 2 Drawing Sheets

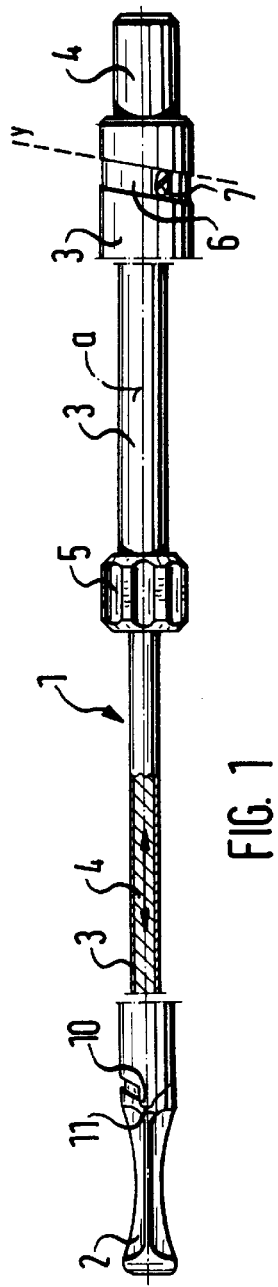
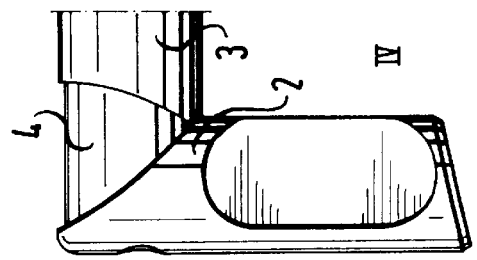
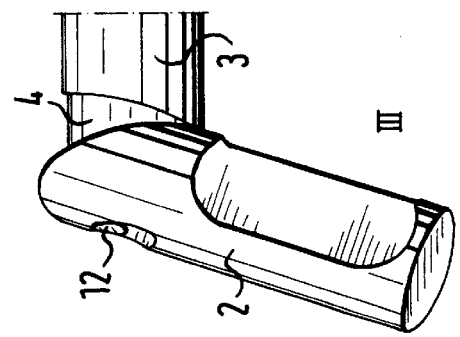
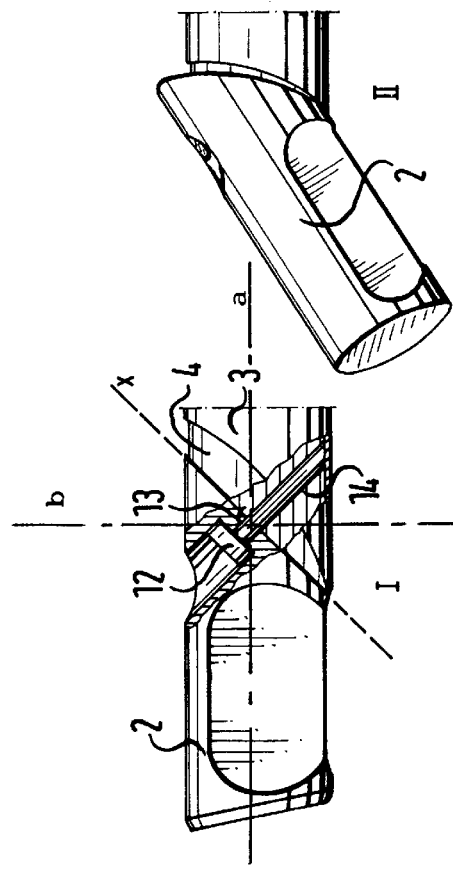

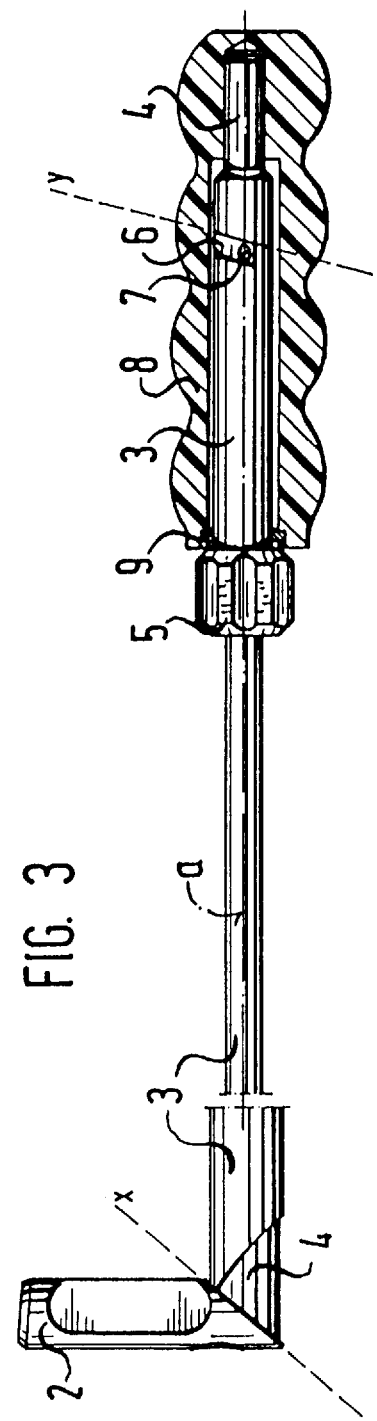
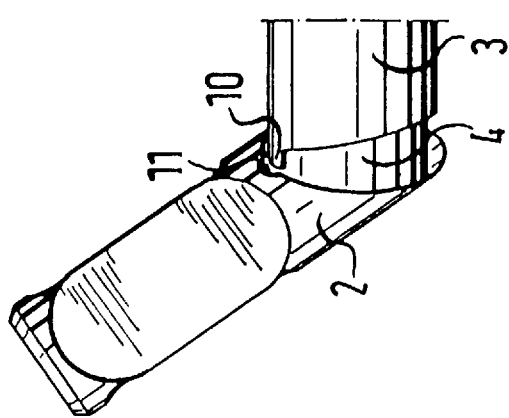

MEDICAL INSTRUMENT WITH A TILTING DISTAL END

FIELD OF THE INVENTION

The invention concerns a medical instrument with a distal end piece which is connected to a holder running through a shank and on operation of a handle, can be adjusted from a rest position into an operating position by tilting relative to the longitudinal axis of the instrument.

BACKGROUND OF THE INVENTION

In surgery, operations are increasingly carried out with instruments which are brought to the operating location by means of a thin cannula. Such instruments are operated from outside the body using a suitable handle, and under observation, e.g by way of an endoscope. In contrast to open surgery, operations are then possible in which the access to the operating location can be provided without large incisions, so that the patient is burdened as little as possible by the operation and the required time for healing can be reduced.

With a few of these operation techniques, the instruments are introduced into the body of the patient by way of very thin cannulas, e.g. Veress-needles, which have a diameter of only 2 or 3 mm. As such, there is often the necessity to tilt the instrument at its distal end after its introduction. Although some instruments with a tiltable distal end are already known, (U.S. Pat. Nos. 518,600, 2,038,394, 2,619, 370 and 5,254,130), with these instruments, the links through which the tilting is effected are provided with rivets, pins or screws, whose loading is limited.

SUMMARY OF THE INVENTION

Against this background, it is the object of the invention to provide a medical instrument of the known type which can be realized in extremely small dimensions, can be guided in the extended condition through a thin cannula, and after passing the cannula can be bought into the tilted working position, as well as having a sufficient stability and a high mechanical loading ability in the extended and bent position.

Since the tiltable end piece and the holder lie facing one another in a plane running inclined to the longitudinal axis of the instrument as well as perpendicular to it, preferably at an angle of 45°, the connection of both parts can be achieved using only one connection element. The dimensions of the connection element can be in the order of the diameter of the shank, and is thus considerably larger than is the case with the previously mentioned instruments of the prior art. In this manner, the connection between the end piece and the holder can be sufficiently mechanically loaded, and their position to one another remains steady during the operation carried out using the instrument. Moreover, it is possible to operate in a more exact and reliable manner with the instrument according to the present invention than with known instruments.

The end piece is designed according to its medical purpose, e.g. as a hook, coagulation probe, needle, stitch fastener, feeler probe and knife, or as a carrier for such instruments. It is advantageous in high frequency applications that all those components which come into contact with the operator are insulated. The insulation can be effected by manufacturing the corresponding parts from ceramics or providing them with a ceramic coating. In the same way, the end piece can be formed partly from ceramics.

The fastening element can be designed for example as a screw or bolt and may be inserted in the end piece using a corresponding bore. In the case that the fastening element is a screw, this is the n screw fastened into a thread on the holder. If on the other hand a bolt is used as the fastening element, its end is inserted into a bore and is fastened therein in a suitable manner, e.g. by welding or adhesive. Alternatively, the screws and bolts can also be inserted through a bore in the holder and fastened to the end piece.

The shank running through from the holder is guidably rotatable and axially adjustable on the holder by way of handle, whereby the axial component of the adjusting movement is given by a guide which is effected in a plane y having the same travel as plane x. Furthermore, the shank and the end piece are connected with a rotational positive fit.

The positive rotational connection is advantageously effected by components attached to the shank and the end piece, and which, in each position of the end piece relative to the holder, i.e in the extended as well as the bent position of the end piece, engage within each other. To this end, the shank may for example be provided with a lug at its distal end which engages in a recess in the end piece.

The positive rotational connection is achieved by the removable positive engagement of the lug in the recess, the lug sliding on one or the other of the edges of the recess, according to the rotational direction. The lug is preferably inclined slightly inwards at its end, such that it can engage in the recess at each position, i.e. irrespective of the angle of the end piece to the longitudinal axis of the instrument.

The holder which is formed as a rod, can be attached at its proximal end to an operating handle engaging at a distance over the proximal part of the shank, and the handle which is rigidly connected to the shank may be provided in the region of the distal end of the operating handle. This solution has the advantage of being able to operate the instrument with one hand, in which for example the thumb and index finger can operate and twist the handle, whilst the other fingers of the hand firmly surround the handle.

The guide may be comprised of a groove formed in the shank and an engaging component attached to the holder and engaging in the groove, said groove running with the same travel as the inclined plane x between the shank and the end piece.

Suitable engagement components may for example be screws or pins as well as raised parts attached to the holder. Alternatively, a groove may be provided on the holder and the engaging component attached to the shank.

BRIEF DESCRIPTION OF THE DRAWINGS

The invention is hereinafter described in more detail by way of the embodiments shown in the drawings. These show:

FIG. 1 a lateral view of the instrument according to the invention, with the end piece located at the rest position, FIGS. 2a to d lateral views of the distal end of the instrument, with the end piece located at four different positions I to IV, FIG. 3 a lateral view of the instrument with a fully tilted end piece corresponding to FIG. 2d and FIG. 4 a different view of the distal end of the instrument, according to FIG. 2c.

DETAILED DESCRIPTION OF THE PREFERRED EMBODIMENT

The instrument 1 comprises essentially of an end piece 2, a shank 3, a holder 4, a handle 3 and a fastening component in the form of a bolt 12.

The shank 3 is firmly attached to the handle 5 and distally of the handle 5 comprises a smaller diameter than proximally. A groove 6 is provided at the proximal end of the shank 3, and into which engages a screw 7 mounted on the holder 4.

As shown in FIG. 3, an operating handle 8 is pushed over the proximal end of the shank 3 and the holder 4, and is firmly attached to the holder 4. For sealing, an O-ring 9 is placed between the operating handle 8 and the shank 3. A lug 10 is mounted on the distal end of the shank 3 and engages into a recess 11 on the end piece 2.

The end piece 2 and the holder 4 lie slidably against each other in a plane x which is incline d at an angle of 45° to the longitudinal axis (a) of the instrument 1 as well as to a perpendicular (b) to the longitudinal axis (a). A bolt 12 is guided perpendicularly to the axis x through a bore 13 in the end piece 2 and a bore 14 in the holder 4, and is firmly attached to said holder 4 for example by screwing or welding, and otherwise runs freely through the bore 13.

On rotation of the shank 3 relative to the fixed holder 4 and the operating handle 8 by way of the handle 5, the end piece 2 connected to the shank 3 via the lug 10 is rotated about the bolt 12 and at the same time, due to its contact with the distal end of the carrier 4 is laterally twisted. Moreover the shank 3 also undergoes proximal or distal movement, depending on the rotational direction of the shank 3, since the groove 6 lies in a plane y having the same travel as plane x and the screw 7 which remains fixed during this procedure, displaces the shank 3 due to its bearing on the one or the other longitudinal sides of the groove 6. The tilting of the end piece 2 which accompanies the increased rotation of the shank 3 is represented in FIGS. 2a to d, whereby position I corresponds to the rest position and positions II to IV corresponds to the various operating positions. In position IV according to FIG. 2d, the end piece 2 is at its maximum tilting with respect to the shank 3. During the whole tilting procedure, of necessity, the lug 10 remains engaged in the recess 11. The same applies for the return tilting to the rest position.

What is claimed is:

1. A medical instrument comprising a distal end piece (2) which is connected to a holder (4) that extends through a shank (3), the shank (3) and the holder (4) having a longitudinal axis (a), a handle (5) is connected to the shank (3) for adjustment of the distal end piece (2) from a rest position to an operating position by tilting relative to the longitudinal axis (a) of the instrument, the end piece (2) and the holder (4) include ends which lie slidably against one another in a plane (x) running inclined to the longitudinal axis (a) as well as to a perpendicular (b) to the longitudinal axis(a), the end piece (2) and the holder (4) are pivotably connected with a fastening element (12) which forms an axis perpendicular to the plane (x), about which the end piece (2) is pivotable relative to the holder (4) upon movement of the handle (5) relative to the holder (4).

2. The instrument according to claim 1, wherein the shank (3) is guidably rotatable and axially adjustable on the holder (4) by movement of the handle (5), the axial component of the adjusting movement is provided by a guide (6, 7) located in a second plane (y) which has an axial travel equivalent to an axial travel of the plane (x), and the shank (3) and the end piece (2) are connected with a rotational positive fit.

3. The instrument according to claim 2, wherein the guide is comprised of a groove (6) formed in the shank (3) and an engaging component (7) attached to the holder (4) which engages in the groove (6), and the groove (6) has the same travel as the inclined plane (x) between the holder (4) and the end piece (2).

4. The instrument according to claim 2, wherein the end piece (2) includes a recess (11) and the shank (3) includes a distal end with a lug (10), and the lug (10) is engaged in the recess (11).

5. The instrument according to claim 2, wherein the holder (4) is formed as a rod which includes a proximal end and a distal end, the shank (3) includes a proximal part, an operating handle (8) having a proximal end and a distal end is attached to the proximal end of the rod and extends over the proximal part of the shank (3), and the handle (5), which is rigidly connected to the shank (3), is located in a region of the distal end of the operating handle (8).

6. The instrument according to claim 1, wherein the end piece (2) includes a recess (11) and the shank (3) includes a distal end with a lug (10), and the lug (10) is engaged in the recess (11).

7. The instrument according to claim 6, wherein the holder (4) is formed as a rod which includes a proximal end and a distal end, the shank (3) includes a proximal part, an operating handle (8) having a proximal end and a distal end is attached to the proximal end of the rod and extends over the proximal part of the shank (3), and the handle (5), which is rigidly connected to the shank (3), is located in a region of the distal end of the operating handle (8).

8. The instrument according to claim 1, wherein the holder (4) is formed as a rod which includes a proximal end and a distal end, the shank (3) includes a proximal part, an operating handle (8) having a proximal end and a distal end is attached to the proximal end of the rod and extends over the proximal part of the shank (3), and the handle (5), which is rigidly connected to the shank (3), is located in a region of the distal end of the operating handle (8).

* * * * *